(12) United States Patent
Abe et al.

(10) Patent No.: US 7,551,710 B2
(45) Date of Patent: Jun. 23, 2009

(54) X-RAY CT APPARATUS AND X-RAY CT IMAGING METHOD

(75) Inventors: Yutaka Abe, Kyoto (JP); Taro Takagi, Hitachi (JP); So Kitazawa, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/968,027

(22) Filed: Oct. 20, 2004

(65) Prior Publication Data

US 2005/0084061 A1 Apr. 21, 2005

(30) Foreign Application Priority Data

Oct. 20, 2003 (JP) ............................. 2003-358648

(51) Int. Cl.
*A61B 6/00* (2006.01)
(52) U.S. Cl. ........................................ 378/10; 378/207
(58) Field of Classification Search ............... 378/4–21, 378/901
See application file for complete search history.

(56) References Cited

U.S. PATENT DOCUMENTS

| | | | | |
|---|---|---|---|---|
| 4,228,356 A | * | 10/1980 | Cushman | 378/39 |
| 4,247,774 A | * | 1/1981 | Brooks | 250/367 |
| 4,422,177 A | * | 12/1983 | Mastronardi et al. | 378/17 |
| 4,788,706 A | * | 11/1988 | Jacobson | 378/207 |
| 5,119,408 A | * | 6/1992 | Little et al. | 378/4 |
| 5,241,576 A | * | 8/1993 | Lonn | 378/19 |
| 5,400,378 A | * | 3/1995 | Toth | 378/16 |
| 5,430,784 A | | 7/1995 | Ribner | |
| 5,450,462 A | * | 9/1995 | Toth et al. | 378/16 |
| 5,696,807 A | * | 12/1997 | Hsieh | 378/109 |

(Continued)

FOREIGN PATENT DOCUMENTS

DE 195 02 574 8/1996

(Continued)

OTHER PUBLICATIONS

Mannudeep et al., Techniques and Applications of Automatic Tube Current Modulation for CT, Radiology, 2004, pp. 649-657.*

(Continued)

*Primary Examiner*—Edward J Glick
*Assistant Examiner*—Alexander H Taningco
(74) *Attorney, Agent, or Firm*—Antonelli, Terry, Stout & Kraus, LLP.

(57) ABSTRACT

An X-ray CT apparatus includes a unit for transmitting an X-ray at not less than two different heights of a measurement object and obtaining a given CT image. Alternatively, the X-ray CT apparatus includes a unit for causing an X-ray to pass through the measurement object and obtaining a CT image and a unit for positioning the X-ray source at not less than two different heights of the measurement object, emitting the X-ray, and obtaining the given CT image. Alternatively, the X-ray CT apparatus includes a unit for causing an X-ray to pass through the measurement object and obtaining a CT image and a unit for obtaining CT image data at a third height position between a first and a second height positions based on CT image data of the first and second height positions of the measurement object.

1 Claim, 10 Drawing Sheets

U.S. PATENT DOCUMENTS

| | | | |
|---|---|---|---|
| 5,875,225 A | 2/1999 | Wallschlaeger | |
| 5,970,112 A * | 10/1999 | Hsieh | 378/8 |
| 6,173,029 B1 * | 1/2001 | Xie et al. | 378/4 |
| 6,198,791 B1 | 3/2001 | He et al. | |
| 6,411,670 B1 * | 6/2002 | Besson | 378/4 |
| 6,470,068 B2 * | 10/2002 | Cheng | 378/20 |
| 6,483,890 B1 * | 11/2002 | Malamud | 378/22 |
| 2001/0028697 A1 | 10/2001 | Nahaliel | |
| 2001/0031033 A1 * | 10/2001 | Toth | 378/19 |
| 2001/0050969 A1 * | 12/2001 | Sembritzki et al. | 378/4 |
| 2003/0058994 A1 * | 3/2003 | Sembritzki | 378/108 |
| 2003/0099323 A1 * | 5/2003 | Nagata et al. | 378/4 |
| 2003/0128807 A1 * | 7/2003 | Kotler et al. | 378/64 |
| 2004/0071258 A1 * | 4/2004 | Okumura et al. | 378/19 |
| 2004/0174948 A1 * | 9/2004 | Kojima et al. | 378/19 |
| 2004/0175034 A1 * | 9/2004 | Wiemker et al. | 382/173 |
| 2004/0247071 A1 * | 12/2004 | Dafni | 378/16 |
| 2005/0002550 A1 * | 1/2005 | Jabri et al. | 382/131 |

FOREIGN PATENT DOCUMENTS

| | | |
|---|---|---|
| EP | 0 549 180 | 6/1993 |
| EP | 0 713 678 | 5/1996 |
| EP | 0 838 784 | 4/1998 |
| EP | 0 982 001 | 3/2000 |
| JP | 62-145375 | 6/1987 |
| JP | 1-124440 | 5/1989 |
| JP | 2-147942 | 6/1990 |
| JP | 6-030922 | 2/1994 |
| JP | 2000-139897 | 5/2000 |
| JP | 2001-330568 | 11/2001 |
| JP | 2001-340330 | 12/2001 |

OTHER PUBLICATIONS

Nonlinear Partial Volume Artifact Correction in Helical CT, Hsieh, IEEE Transactions of Nuclear Science, col. 46, No. 3, Jun. 1999.
Nonlinear Partial Volume Artifacts in X-ray Computer Tomography, Glover, Am. Assoc, Phys. Med, Man/Jun. 1980.
Reduced Partial Volume Artifacts Using Spiral Computed Tomography and an Integrating Interpolator, Heuscher et al, Med. Phys. 26 (2) Feb. 1999.
"Image Processing Algorithm," published by Kindaikagakusha, ppgs. 106-111 (in Japanese).
Japanese Office Action dated May 29, 2007.

* cited by examiner

X-RAY CT APPARATUS AND X-RAY CT IMAGING METHOD

BACKGROUND OF THE INVENTION

The present invention relates to an X-ray CT apparatus and an X-ray CT imaging method.

Imaging techniques using X-ray CT apparatuses to construct three-dimensional images are disclosed in JP-A-2001-330568 and others.

SUMMARY OF THE INVENTION

The imaging techniques using conventional X-ray CT apparatuses are not devised in consideration of an error in the height direction in the construction of a three-dimensional image.

An object of the present invention is to provide an X-ray CT apparatus and an X-ray CT imaging method that can reduce a measuring error in the height direction regardless of a measurement object.

In the X-ray CT apparatus, X-rays are transmitted at least two different heights of a measurement object to obtain a given CT image.

The present invention makes it possible to provide an X-ray CT apparatus and an X-ray CT imaging method that can reduce a measuring error in the height direction regardless of a measurement object.

Other objects, features and advantages of the invention will become apparent from the following description of the embodiments of the invention taken in conjunction with the accompanying drawings.

DESCRIPTION OF THE INVENTION

Nondestructive internal three-dimensional measurements have grown in demand. Industrial X-ray CT apparatuses achieving CT images with highly accurate dimensional measurements are indispensable to satisfy the needs. The following apparatus is desirable: three-dimensional bit map data of a measurement object is obtained using an X-ray CT imaging apparatus, an image is displayed according to the three-dimensional bit map data, and a measurement probe is caused to scan along a scanning path defined for the image to measure the dimensions of the measurement object, so that dimensional measurements are performed with high accuracy. The three-dimensional bit map data is solid data representing the three-dimensional measurement object, which is constituted of pixels (voxels) of a cube or a rectangular solid. Each voxel has information (CT value) on an attenuation factor at the voxel of the measurement object.

It is desirable in dimensional measurements that a CT value obtained by the X-ray CT apparatus is proportionate to an average attenuation factor of the measurement object having the voxels. On the assumption that a CT value is proportionate to an average attenuation factor of the measurement object, a technique is considered to estimate the boundary position of the measurement object based on a spatial change of the CT value of a voxel around a boundary surface. However, when dimensional measurements are performed on the measurement object in the height direction, the boundary surface of substances having different attenuation factors frequently becomes almost parallel with a slice surface. Thus, regarding voxels including such a boundary surface, it is difficult to establish proportionality between a CT value and an average attenuation factor due to nonlinear partial volume effect. For this reason, it is difficult for the foregoing technique to perform highly accurate dimensional measurements when performing dimensional measurements on a measurement object in the height direction. The nonlinear partial volume effect will be discussed later.

An embodiment of the present invention will describe an improved technique for obtaining a CT value proportionate to an average attenuation factor even when a voxel includes a boundary surface almost parallel with a slice surface.

The following will describe an embodiment of an X-ray CT apparatus and imaging method according to the present invention with reference to the accompanying drawings.

Figure 1:
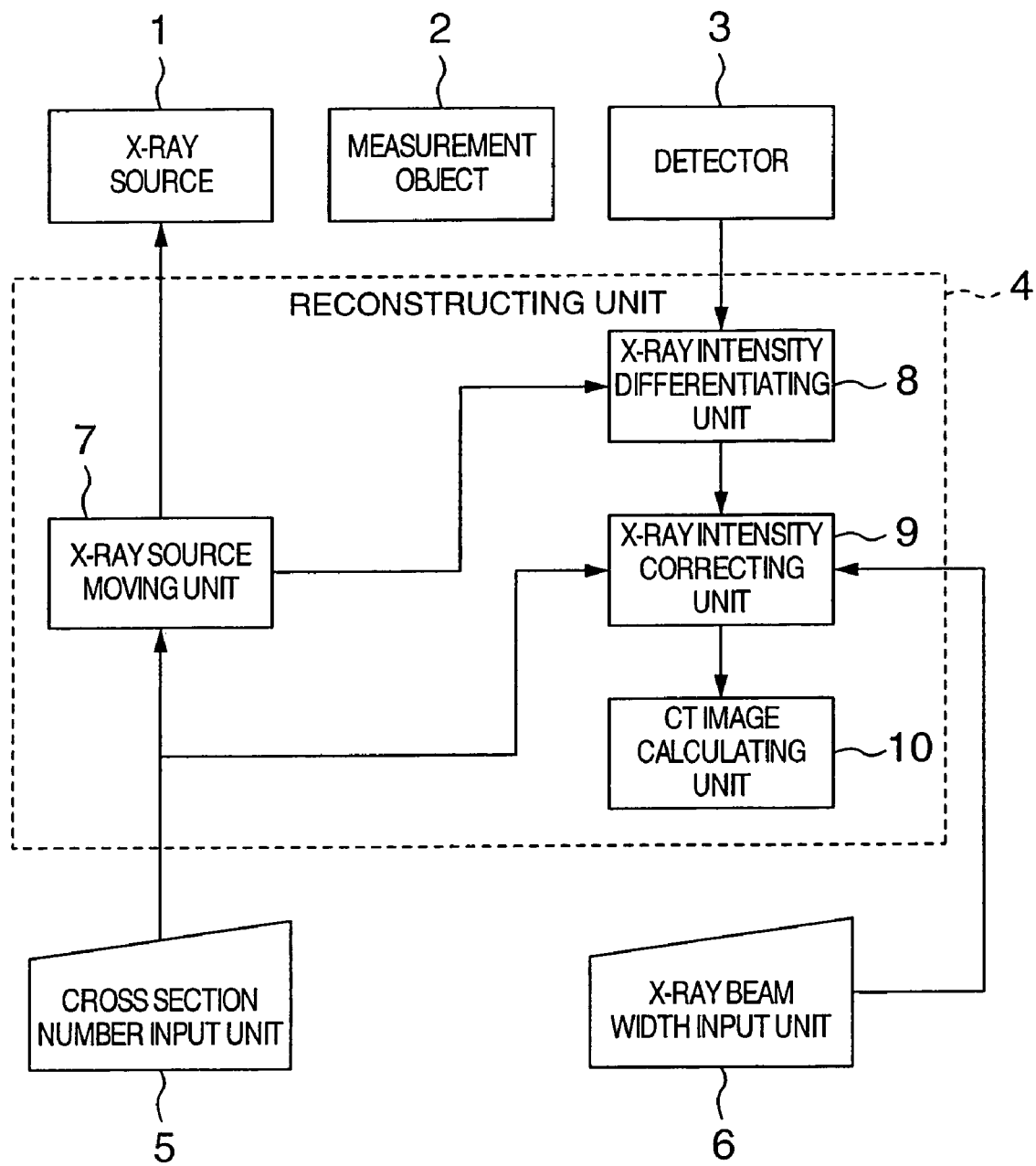
FIG. 1 is a structural diagram showing an X-ray CT apparatus according to an embodiment of the present invention.

FIG. 1 is a diagram showing the schematic configuration of an industrial X-ray CT apparatus according to an embodiment of the present invention. The X-ray CT apparatus comprises an X-ray source 1 for generating an X-ray to be emitted to a measurement object 2, a detector 3 for measuring an X-ray having passed through the measurement object 2, a reconstructing unit 4 for reconstructing a CT image of the measurement object 2 according to the intensity of the X-ray having passed through the measurement object 2, a cross section number input unit 5 for inputting to the reconstructing unit 4 the number of cross sections imaged when one CT image is reconstructed, and an X-ray beam width input unit 6 for inputting to the reconstructing unit 4 a beam width of an X-ray passing through the measurement object 2. Here, the height indicates a position in a direction perpendicular to a slice surface, and the beam width of the X-ray indicates a width of an X-ray beam in the height direction.

The X-ray source 1 is constituted of an accelerator, a target, a pre-collimator and so on and has the function of generating an X-ray to be emitted to the measurement object 2. The X-ray source 1 accelerates electrons at a predetermined voltage by using an accelerator. Thereafter, the X-ray source 1 collides the electrons with a target of a thin metal plate and generates an X-ray by using bremsstrahlung. The pre-collimator disposed at the front of the target is made of a material such as lead and tungsten, which resist the passage of an X-ray, and has a window, from which an X-ray is emitted, only toward the measurement object 2. In this way, the X-ray source 1 can emit an X-ray, which is gathered like a beam, to the measurement object 2.

The detector 3 is positioned on the opposite side from the X-ray source 1 with the measurement object 2 being interposed between the detector 3 and the X-ray source 1, and is constituted of a plurality of radiation detectors, a collimator, and so on. Further, the detector 3 has the function of measuring the intensity of an X-ray having passed through the measurement object 2. The radiation detectors in the detector 3 are arranged in a matrix form so as to face the window of the pre-collimator of the X-ray source 1 and output a signal corresponding to the detected X-ray intensity. At this point, the collimator is disposed on the front or side of the radiation detector to intercept a scattered X-ray and an X-ray having passed through an adjacent radiation detector.

The reconstructing unit 4 is constituted of an X-ray source moving unit 7 for moving the X-ray source 1 and the detector 3 in the height direction, an X-ray intensity differentiating unit 8 for calculating a rate of change in the intensity of an X-ray in the height direction, the X-ray intensity being measured by the detector 3, an X-ray intensity correcting unit 9 for correcting the intensity of an X-ray at a certain (single) height, and a CT image calculating unit 10 for calculating a CT image according to the corrected X-ray intensity. The reconstructing unit 4 has the function of reconstructing a CT image of the measurement object 2 according to an X-ray intensity measured by the detector 3. The X-ray source moving unit 7 has the function of, when one CT image is obtained, moving the X-ray source 1 and the detector 3 to image the measurement object 2 as many as the number (at least two) specified by the cross section number input unit 5. The X-ray intensity differentiating unit 8 has the function of calculating a rate of change in the intensity of an X-ray in the height direction according to the X-ray intensity measured by the detector 3 and the height position of the X-ray source 1, the height position being obtained by the X-ray source moving unit 7. The X-ray intensity correcting unit 9 has the function of correcting the intensity of an X-ray at a certain height by using X-ray intensities at two or more heights, rates of change of the X-ray intensities, and a beam width of an X-ray that is provided from the X-ray beam width input unit 6. The CT image calculating unit 10 has the function of performing integration called a convolution integral on the corrected X-ray intensity and calculating a CT image at a certain height. In this way, there are provided units for positioning the X-ray source 1 at least two different heights of the measurement object 2 and emitting an X-ray to obtain a given CT image. Thus, it is possible to reduce a measuring error in the height direction of the X-ray CT apparatus regardless of a measurement object (even if a measurement object has different attenuation factors).

The reconstruction of a CT image is specifically described in "Image Processing Algorithm"(published by Kindaikagakusha) and others. The cross section number input unit 5 inputs to the reconstructing unit 4 the number of cross sections imaged when a CT image is reconstructed. The X-ray beam width input unit 6 inputs to the reconstructing unit 4 a beam width of an X-ray passing through the measurement object 2.

According to the X-ray CT apparatus of the present embodiment, it is possible to properly reduce a measuring error in the height direction of the X-ray CT apparatus with ease. Even when the boundary surface of a measurement object becomes almost parallel with a slice surface in dimensional measurements in the height direction, it is possible to obtain a CT value proportionate to an attenuation factor of the measurement object.

Figure 2:
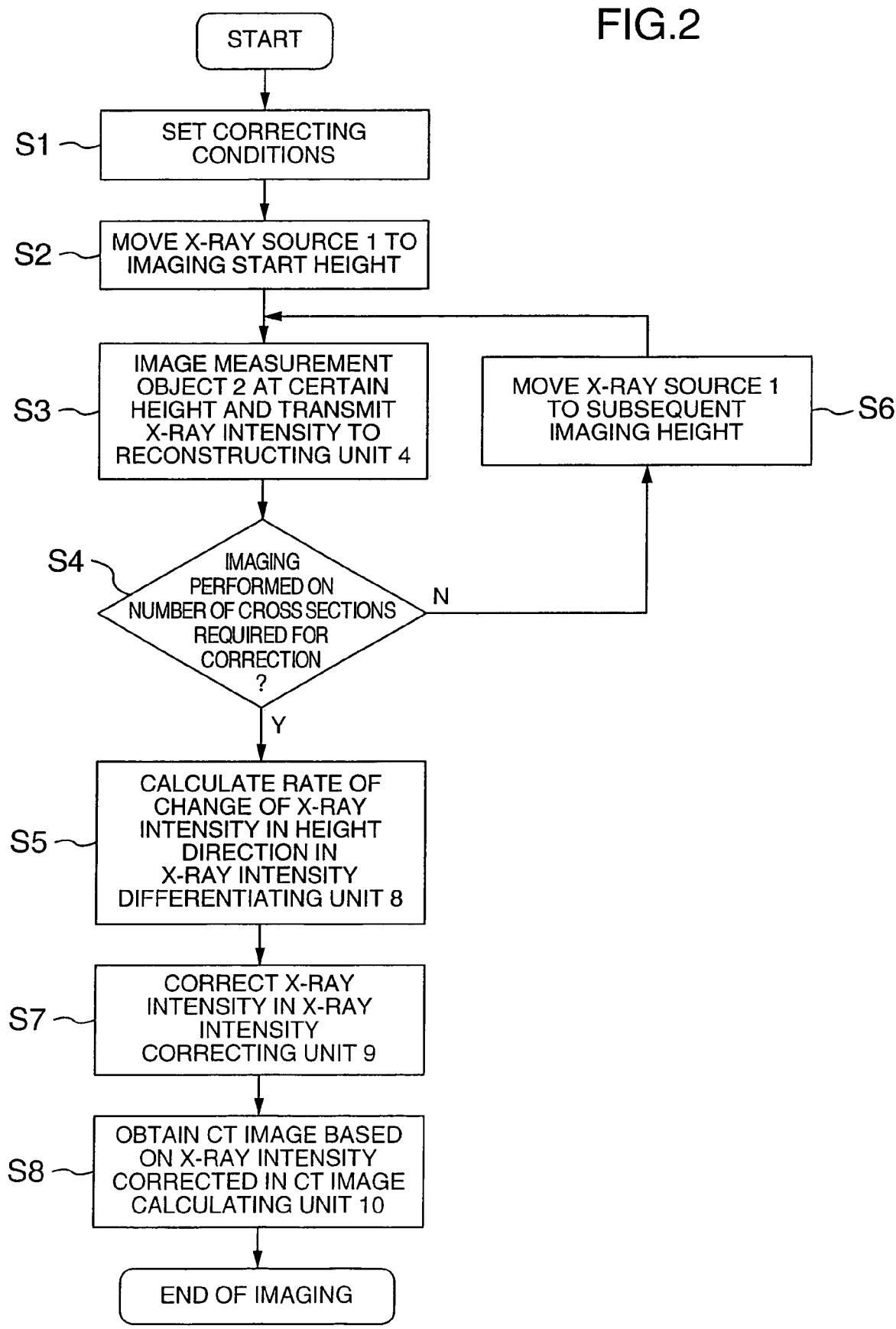
FIG. 2 is a flowchart showing the operations of the X-ray CT apparatus according to the present invention.
Figure 3:
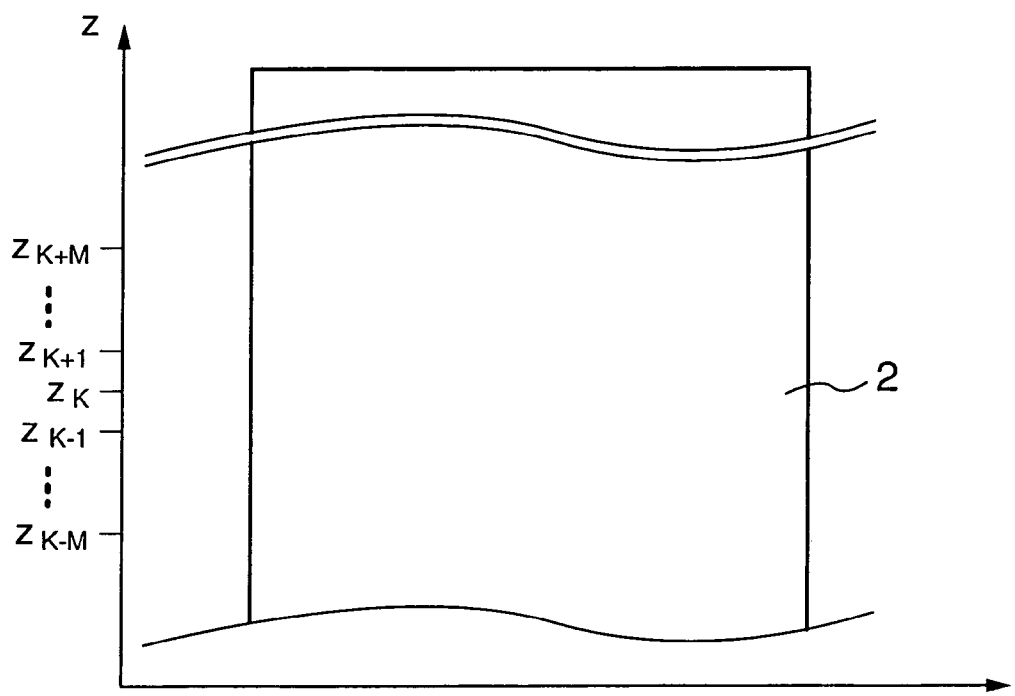
FIG. 3 is a side view showing heights where imaging is actually performed to obtain a CT image in the X-ray CT apparatus of the present invention.

Referring to FIGS. 2 and 3, the operations of the X-ray CT apparatus will be described below. FIG. 2 is a flowchart showing the operations of the X-ray CT apparatus. FIG. 3 is a side view showing heights where imaging is actually performed to obtain one CT image.

The X-ray CT apparatus of the present embodiment is characterized in that an X-ray intensity at a height where a CT image is obtained is corrected according to X-ray intensities at two or more upper and lower heights of the image and a CT image is reconstructed using the corrected X-ray intensity. Hence, the measurement object 2 is imaged at a plurality of heights to obtain one CT image. The present embodiment will discuss an example where 2M+1 cross sections are imaged from heights $z_{K-M}$ to $z_{K+M}$ in this order to obtain a CT image at a height $z_K$ shown in FIG. 3.

First, correcting conditions are set in step S1. Items to be set are the number of cross sections used for correction and a width of an X-ray beam. These values are inputted to the reconstructing unit 4 by the cross section number input unit 5 and the X-ray beam width input unit 6. The way to set these values will be described later. In subsequent step S2, the X-ray source moving unit 7 moves the X-ray source 1 and the detector 3 to the imaging start position $z_{K-M}$. In subsequent step S3, the measurement object 2 is rotated while being irradiated with an X-ray from the X-ray source 1, and an X-ray intensity measured by the detector 3 is transmitted to the reconstructing unit 4.

In subsequent step S4, it is decided whether imaging has been performed as many as the number of cross sections set in step S1. When the necessary number of cross sections has not been imaged, the process advances to step S6, the X-ray source 1 and the detector 3 are moved to a subsequent imaging height, and the process returns to step S3 to image the measurement object 2. These operations are repeated until the number of imaged cross sections reaches 2M+1.

When the number of imaged cross sections reaches 2M+1, the process advances from step S4 to step S5 and the X-ray intensity differentiating unit 8 calculates a rate of change of the X-ray intensity in the height direction. A rate of change is calculated for X-ray intensities measured at all irradiation angles by all the radiation detectors constituting the detector 3.

In step S7, the X-ray intensity correcting unit 9 corrects an X-ray intensity at the height $z_K$ based on the X-ray intensity, a rate of change of the X-ray intensity in the height direction, and the beam width of the X-ray. The correcting method will be described later. In step S8, the CT image calculating unit 10 calculates a CT image at the height $z_K$ according to the corrected X-ray intensity. The operations of X-ray CT according to the present invention are performed as described above. In this way, there are provided the unit for causing an X-ray emitted from the X-ray source 1 to pass through the measurement object 2 and obtaining a CT image, and the unit for obtaining CT image data at a third height position ($z_K$) between a first height position and a second height position based on CT image data at the first height position and the second height position of the measurement object 2. Hence, it is possible to reduce a measuring error in the height direction of the X-ray CT apparatus regardless of the measurement object 2 (even if the measurement object has different attenuation factors).

Figure 4:
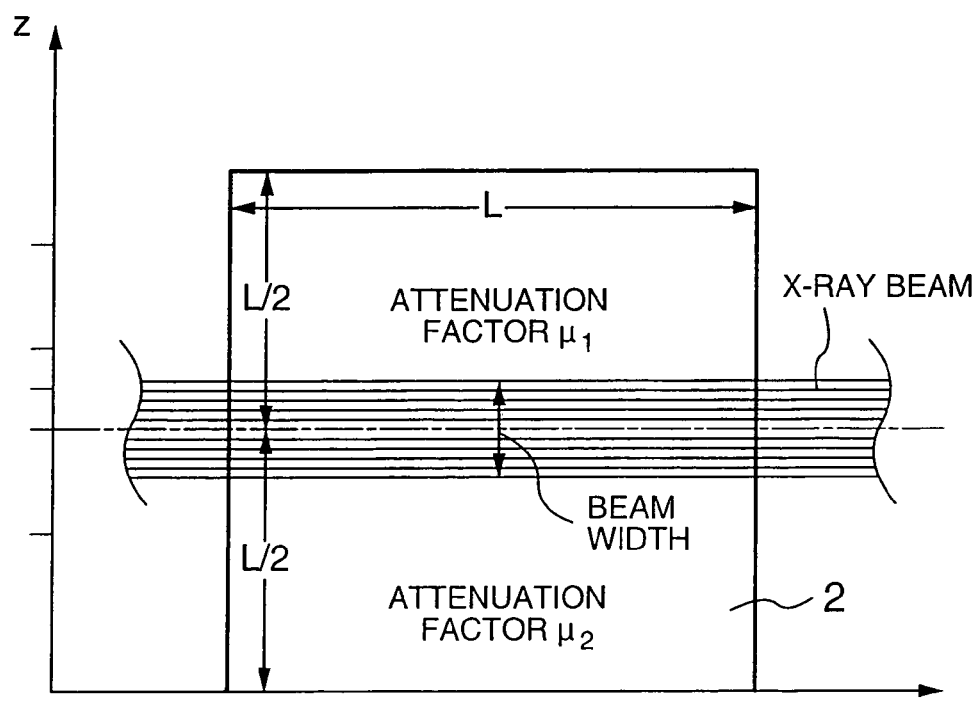
FIG. 4 is a side view showing that imaging is performed on a boundary surface of a measurement object 2, which is a cube having two different attenuation factors.

Referring to FIG. 4, correction performed by the X-ray intensity correcting unit 9 will be described below. FIG. 4 is a side view showing that imaging is performed on a boundary surface of the cubic measurement object 2 which has two different attenuation factors. On the assumption that a CT value and an average attenuation factor are proportionate to each other, when the position of the boundary surface is determined according to a spatial change of a CT value to measure the dimensions of the measurement object 2, the CT value and the average attenuation factor are not proportionate to each other in dimensional measurements in the height direction due to nonlinear partial volume effect. This is regarded as the cause of a measuring error in dimensional measurements in the height direction. The X-ray CT apparatus of the present embodiment comprises the X-ray intensity correcting unit 9 to correct the nonlinear partial volume effect.

The following will discuss the nonlinear partial volume effect in the imaging of the measurement object 2 shown in FIG. 4. The measurement object 2 is a cube where a side has a length of L, and the measurement object 2 is made of two substances such that the upper part has an attenuation factor $\mu_1$ and the lower part has an attenuation factor $\mu_2$. FIG. 4 shows that the boundary surface of the two substances is imaged by an X-ray having a finite width. The center of the X-ray beam is positioned on the boundary surface. When an incident X-ray has an intensity of $I_0$, a transmitted X-ray has an intensity I expressed by the formula below:

$$I = \{\exp(-\mu_1 L) + \exp(-\mu_2 L)\} I_0 / 2 \quad (1)$$

Since the X-ray beam has a finite width, the upper part and the lower part of the X-ray beam have different attenuation factors in a transmission path. Hence, I is the sum of intensities of the X-rays passing through the part of the attenuation factor $\mu_1$ and the part of the attenuation factor $\mu_2$. An effective attenuation factor $\mu_e$ is defined by the formula below:

$$I_0 \exp(-\mu_e L) = I \quad (2)$$

In this case, I represents an intensity attenuated by a substance having an attenuation factor of $\mu_e$.

$$\mu_e = -(1/L) \times \ln[\{(\exp(-\mu_1 L) + \exp(-\mu_2 L)\} / 2] \quad (3)$$

In the reconstruction theory of an X-ray CT image, the attenuation of I is expressed by a single exponential function like formula (2). Hence, a CT value obtained by reconstruction is proportionate to $\mu_e$.

The measurement object 2 in the transmission path of an X-ray shown in FIG. 4 has an average attenuation factor $\mu_m$ expressed by the formula below:

$$\mu_m = (\mu_1 + \mu_2) / 2 \quad (4)$$

Since $\mu_1 \neq \mu_2$ is established on the boundary surface, it is found from formulas (3) and (4) that $\mu_e$ and $\mu_m$ are not equal to each other and a ratio of the attenuation factors changes nonlinearly depending on $\mu_1$ and $\mu_2$. Thus, the CT value obtained by reconstruction is not proportionate to $\mu_m$. In this way, since the X-ray beam has a finite width, the CT value is not proportionate to the average attenuation factor $\mu_m$. Such a phenomenon is called nonlinear partial volume effect. Particularly when the slice surface and the boundary surface are parallel with each other as shown in FIG. 4, this effect is enhanced.

In order to correct the nonlinear partial volume effect, the measured X-ray intensity I is corrected to an X-ray intensity $I_m$ which is obtained during the passage of a substance having the average attenuation factor $\mu_m$, and a CT image is reconstructed using $I_m$. The X-ray intensity $I_m$ is expressed by the formula below:

$$I_m = I_0 \exp(-\mu_m L) \quad (5)$$

Hence, the reconstructing unit 4 comprises the X-ray intensity correcting unit 9 as a preprocessing unit of the CT image calculating unit 10.

In FIG. 4, a correction formula from I to $I_m$ is derived as below from formula (2) and formula (5).

$$I_m = \{I/I_o^{(1-\mu e/\mu m)}\}^{\mu m/\mu e} \quad (6)$$

For simple explanation, on the assumption the upper part of the cube is an air layer and $\mu_1 = 0$ is established, a correction formula is derived as below:

$$I_m = I_o \{(2I - I_o)/I_o\}^{1/2} \quad (7)$$

Formula (7) is a correction formula which is only applicable to the measurement object 2 having the shape and attenuation factors shown in FIG. 4.

Figure 5A:
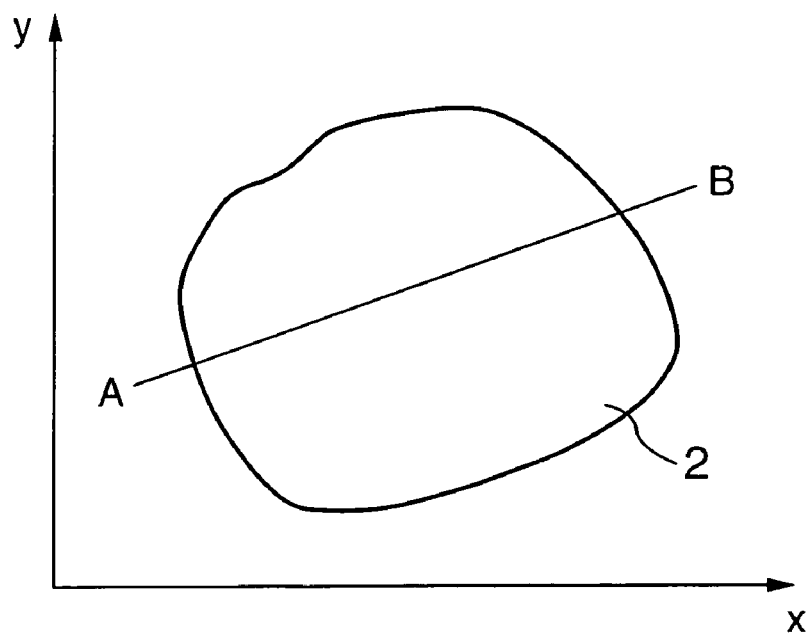
FIG. 5A is an elevation showing a certain measurement object 2.
Figure 5B:
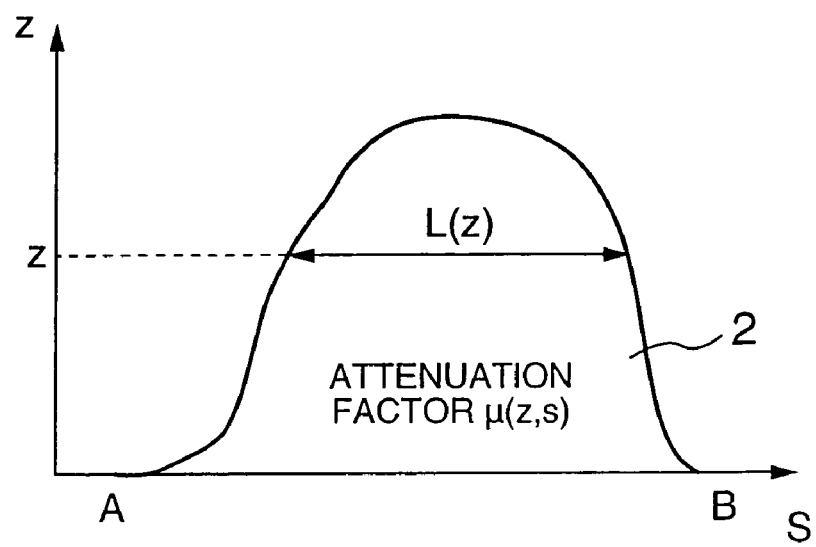
FIG. 5B is a sectional view taken along line AB of the measurement object 2.

In general, the shape and attenuation factors of the measurement object 2 can be arbitrarily set. Thus, these amounts are estimated based on a rate of change of the X-ray intensity in the height direction and the X-ray intensity is corrected based on the estimated amounts. Referring to FIGS. 5A and 5B, the correcting method will be schematically explained below.

FIG. 5A is an elevation showing a certain measurement object 2. FIG. 5B is a sectional view taken along line AB of the measurement object 2. In this sectional view, z represents a height, $\mu(z, s)$ represents an attenuation factor of the measurement object 2 at coordinates s on line AB, and L(z) represents a length of the measurement object 2 at the height z.

Figure 6:
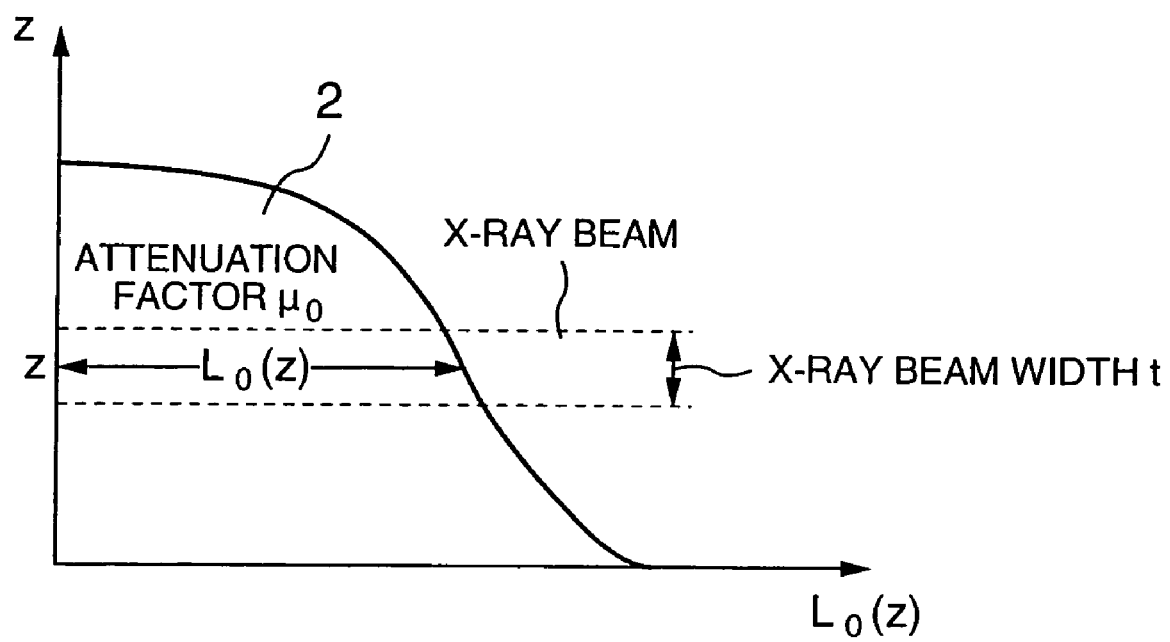
FIG. 6 is a sectional view taken along line AB when the attenuation factor of the measurement object 2 shown in FIGS. 5A and 5B is replaced with $\mu_0$.

If the attenuation factor of the measurement object 2 is replaced with a constant value $\mu_0$, a cross section taken along line AB is obtained as shown in FIG. 6. In this case, in the cross section of FIG. 6, a length $L_e(z)$ of the measurement object 2 at the height z satisfies the following conditional expression (8):

$$\int \mu(z,s) L(z) ds = \mu_0 L_e(z) \quad (8)$$

In this case, in FIGS. 5A and 5B and FIG. 6, an X-ray passing through the measurement object 2 has a constant intensity.

In FIG. 6, it is assumed that an X-ray beam having an intensity of $I_0$ passes through the object at the height z. The X-ray beam has a width of t. In this case, since the measurement object has an average attenuation factor of $\mu_0$, an average transmitting distance $L_m(z)$ of the X-ray beam is defined as formula (9) below:

$$L_m(z) = \frac{1}{t} \int_{z-t/2}^{z-t/2} L_e(z') dz' \quad (9)$$

According to this definition, like formula (5), an X-ray passing through a substance having the average attenuation factor has an intensity $I_m$ expressed by the formula below:

$$I_m = I_o \exp(-\mu_0 L_m(z)) \tag{10}$$

$\mu_0$ and $L_m(z)$ can be determined by the beam width of the X-ray, X-ray intensities measured by the detector 3 at two or more heights including the height z in the vertical direction, and a rate of change in intensity in the height direction. A CT image is reconstructed using $I_m$ in the CT image calculating unit 10.

The above described correction is performed on X-ray intensities measured at all irradiation angles by all the radiation detectors constituting the detector 3. By reconstructing a CT image based on the corrected X-ray intensities, it is possible to obtain a CT value proportionate to the average attenuation factor.

The following will discuss the way to set the number of cross sections for correction and a width of an X-ray beam. The setting is made in step S1 of FIG. 2.

In general, a larger number of cross sections results in a greater correcting effect. However, imaging and correction take a longer time. In this way, the correcting effect and a time for imaging are mutually contradictory and thus it is desirable to properly set these values according to the measurement object 2.

Correction is particularly necessary in an area where an X-ray intensity rapidly changes in the height direction, for example, in the case where the boundary surface of two substances having different attenuation factors is imaged as shown in FIG. 4. Conversely, when a transmitted X-ray makes a small change in intensity in the height direction in an imaging range, correction becomes less necessary. In the present embodiment, the number of cross sections used for correction can be determined and set properly based on a rate of change of the X-ray intensity in the imaging range. For example, the number of cross sections can be inputted by the cross section number input unit 5. That is, the cross section number setting unit is provided for setting the number of different height positions for imaging the measurement object 2, thereby properly setting the number of cross sections and processing time. That is, in the X-ray CT apparatus of the present embodiment for obtaining a CT image at a given height based on CT image data at not less than two different heights of the measurement object 2, a position measurement number setting unit is provided for setting the number of measurements at different heights, thereby enabling the user to properly use the apparatus in view of imaging time and accuracy. In addition to the position measurement number setting unit for setting the number of measurements at different height positions, a unit is provided for displaying imaging time and measuring accuracy according to the number of measurements. The number of measurements is set by the position measurement number setting unit. Thus, it is possible to confirm imaging time and measuring accuracy beforehand, which correspond to the number of measurements, and make a proper selection, thereby efficiently using the apparatus with ease. Further, the user can select whether imaging time or measuring accuracy should have higher priority according to the number of measurements.

Figure 7:
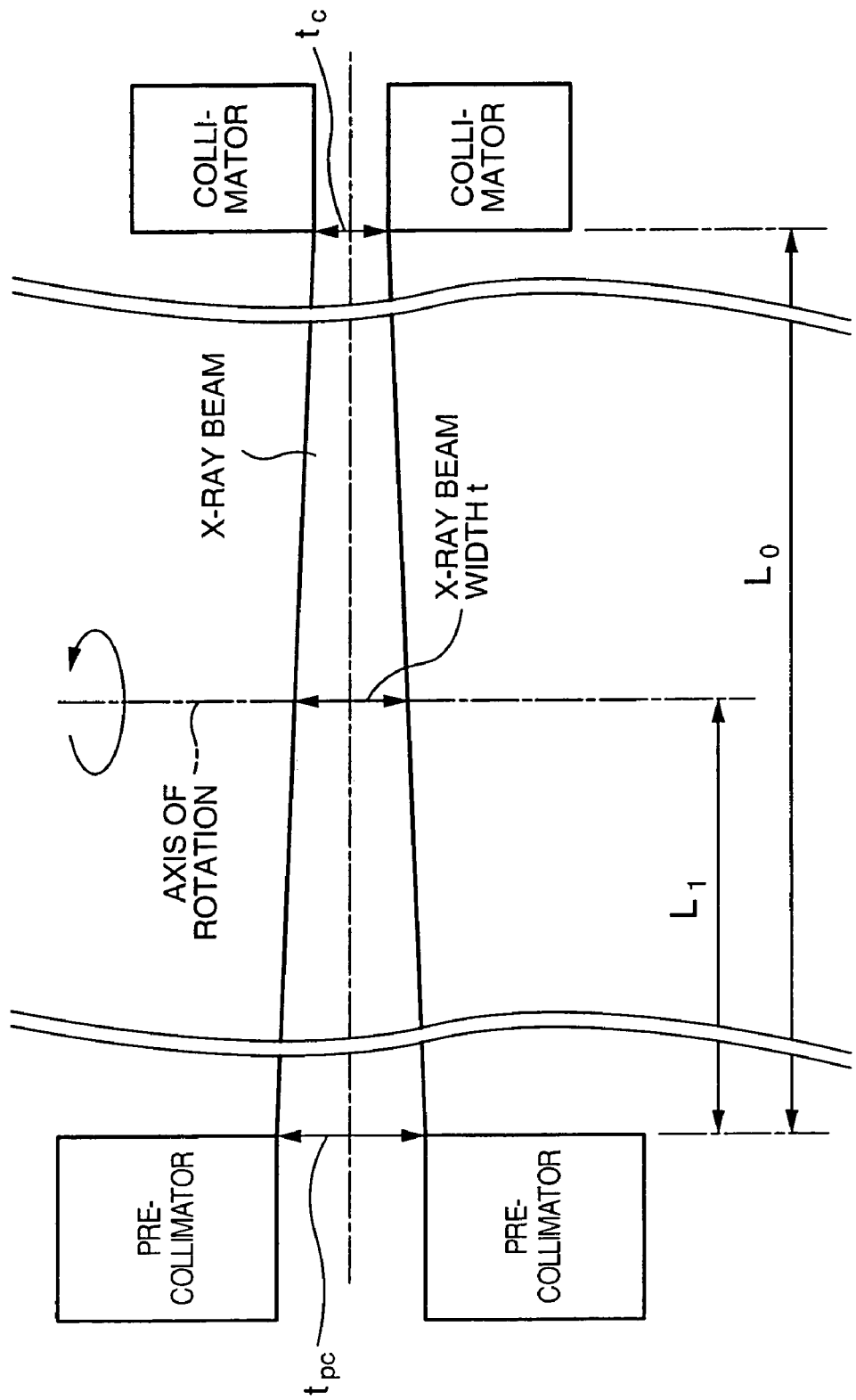
FIG. 7 is a side view showing a geometric relationship between an X-ray beam width and pre-collimators and collimators.

Referring to FIG. 7, which is a side view showing the X-ray source 1 and the collimators of the detector 3, a method of setting a width of an X-ray beam will be discussed below. The width of the X-ray beam indicates a height of the X-ray beam at the center of rotation of the measurement object 2. A width t of the X-ray beam is geometrically determined by the formula below:

$$t = t_{pc} + (t_c - t_{pc}) L_1 / L_0 \tag{11}$$

$t_{pc}$ represents a height of the window on the pre-collimator of the X-ray source 1, $t_c$ represents a height of a window on the collimator set at the front of each radiation detector of the detector 3, $L_1$ represents a distance between the pre-collimator and the collimator, and $L_0$ represents a distance between the pre-collimator and the axis of rotation. The user inputs this value from the X-ray beam width input unit 6.

Figure 8:
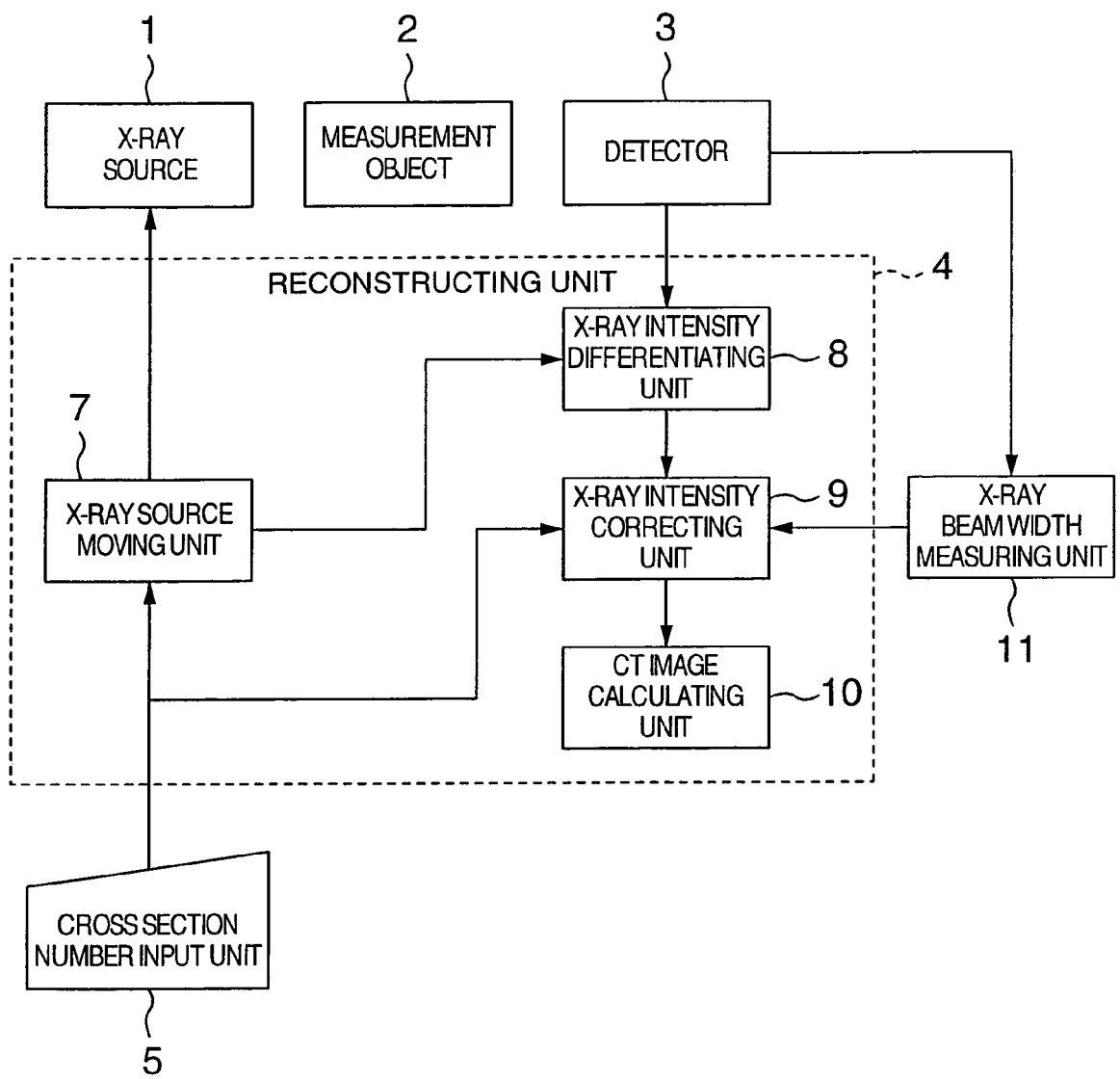
FIG. 8 is a structural diagram showing an X-ray CT apparatus according to another configuration of the present invention.

Alternatively, the following method may be used instead of formula (11): an image of an object having a known shape such as a cylinder is photographed in the height direction, and the width of an X-ray beam is measured based on a change in X-ray intensity measured by the detector 3. Referring to FIG. 8 showing the X-ray CT apparatus having another configuration, this method will be discussed below. In this configuration, the X-ray CT apparatus comprises an X-ray beam width measuring unit 11 instead of the X-ray beam width input unit 6 of FIG. 1.

Figure 9:
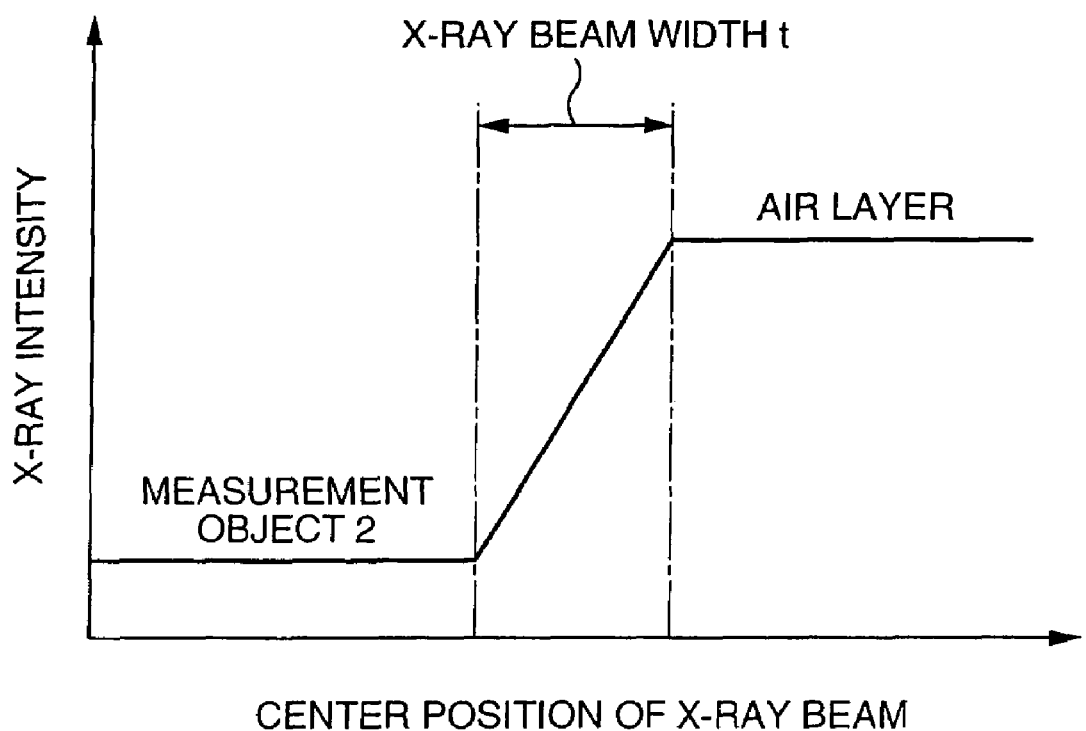
FIG. 9 shows an X-ray intensity obtained by imaging the upper end face of a cylinder in the height direction.
Figure 10A:
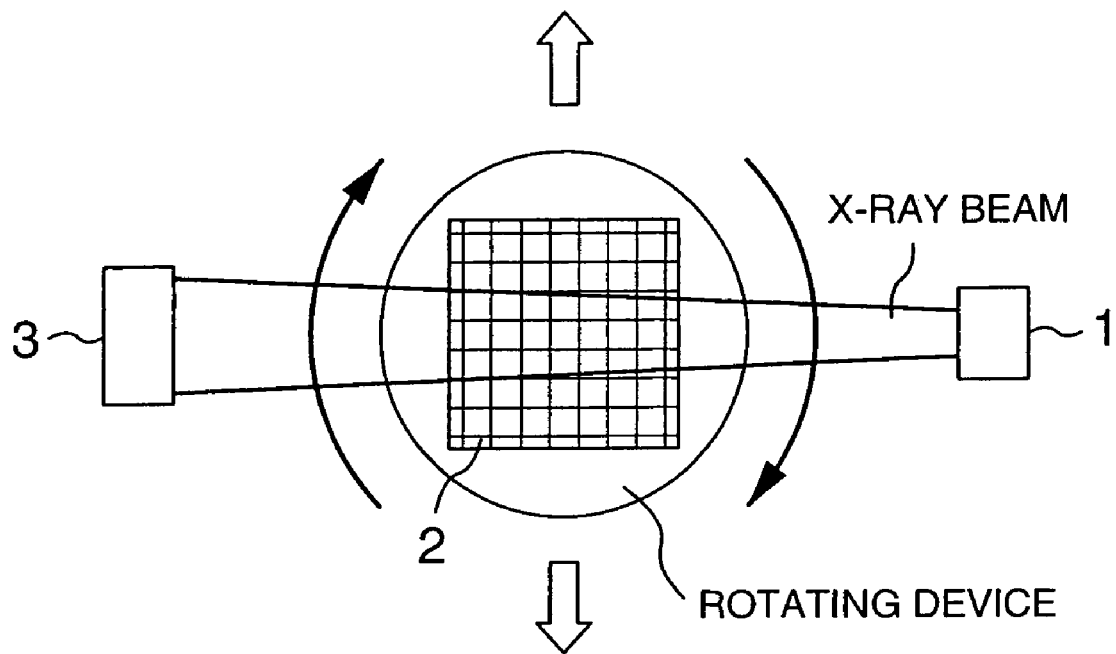
FIG. 10A is an elevation showing the schematic configuration of an X-ray CT apparatus of a second-generation system.
Figure 10B:
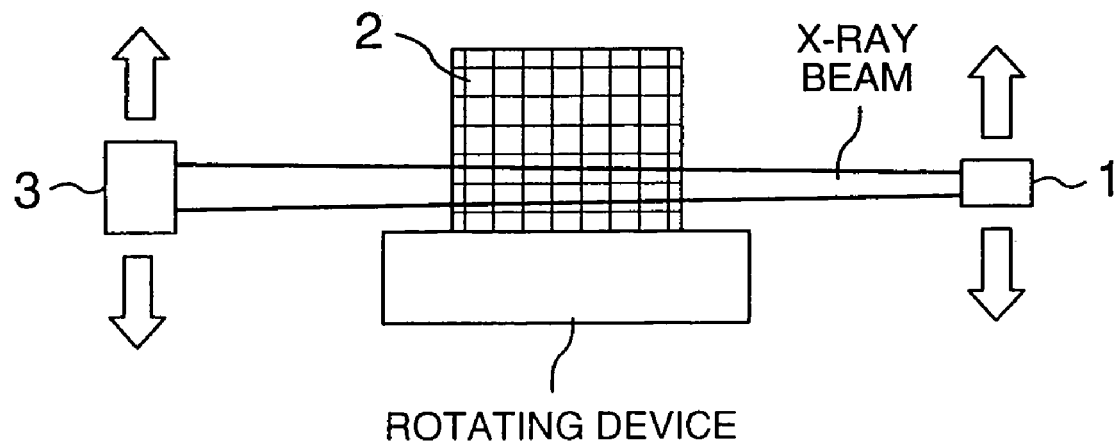
FIG. 10B is a side view showing the configuration.
Figure 11A:
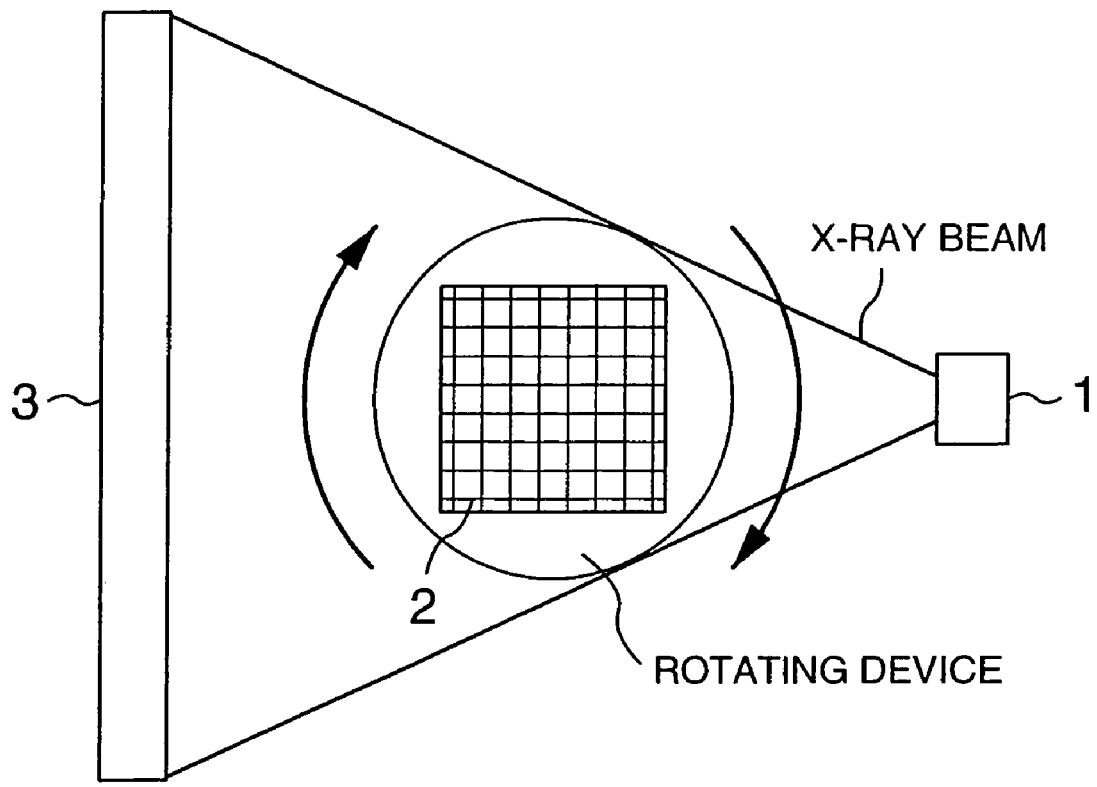
FIGS. 11A and 11B have an elevation and a side view showing the schematic configuration of an X-ray CT apparatus of a multislice system.
Figure 11B:
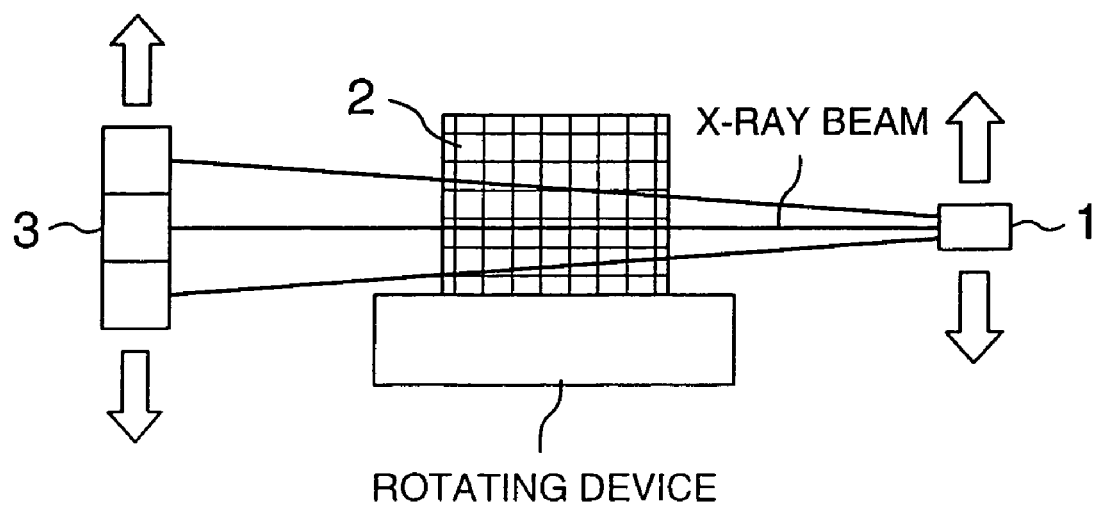

When the X-ray source 1 and the detector 3 are moved by the X-ray source moving unit 7 and imaging is performed around the upper end face of the cylindrical measurement object 2, an X-ray intensity is measured in one of the radiation detectors of the detector 3 as shown in FIG. 9. When an X-ray beam only passes through the measurement object 2 or an air layer, an X-ray intensity becomes constant. When an X-ray beam passes through both of the measurement object 2 and an air layer, an X-ray intensity is changed according to a volume ratio of the measurement object 2 and the air layer in the transmission path of an X-ray beam. Therefore, as shown in FIG. 9, it is possible to determine a width of an X-ray based on a length permitting a change of an X-ray intensity. The X-ray beam width measuring unit 11 performs the above described processing using the X-ray intensity measured by the detector 3 and transmits the beam width of the X-ray to the X-ray intensity correcting unit 9. The width of an X-ray beam emitted from the X-ray source is inputted by the X-ray beam width input unit 6 and information on the width of the X-ray beam can be provided to the X-ray intensity correcting unit 9, thereby further improving measuring accuracy. Moreover, since the X-ray beam width measuring unit 11 is provided as a unit for measuring an amount of a beam width of an X-ray, it is possible to accurately measure the width of an X-ray beam emitted from the X-ray source and provide accurate information on the width of the X-ray beam for the X-ray intensity correcting unit 9, thereby further improving measuring accuracy.

By using the amount of the width of the X-ray in the X-ray intensity correcting unit 9, it is possible to correct an error in dimensional measurements, the error being caused by the beam width of the X-ray in the height direction, and thus measuring accuracy can be further improved.

In this way, in the X-ray CT apparatus of the present embodiment for obtaining a CT image at a given height based on CT image data at not less than two different heights of the measurement object, a beam width setting unit is provided for setting data on a beam width of an X-ray used for measurements. Thus, it is possible to properly confirm and set a width of a beam and properly set processing time. Further, the user can properly use the apparatus in view of imaging time and accuracy. In addition to the beam width setting unit for setting data on a beam width of an X-ray used for measurements, a unit is provided for displaying imaging time and measuring accuracy according to a beam width set by the beam width setting unit. Thus, it is possible to confirm imaging time and measuring accuracy beforehand, which correspond to the number of measurements, and make a proper selection, thereby efficiently using the apparatus with ease. Further, the user can select whether imaging time or measuring accuracy should have higher priority according to the beam width of the X-ray.

When the X-ray source 1 is exchanged, an X-ray beam changes in width. Hence, the process has to include an operation of estimating or measuring a beam width of the X-ray. Since the unit for inputting a beam width of an X-ray or the unit for measuring a beam width of an X-ray is provided, even when the X-ray source 1 is exchanged, it is possible to provide the X-ray intensity correcting unit 9 with a width of an X-ray beam emitted from a newly provided X-ray source 1.

The above describe embodiment described a third-generation X-ray CT apparatus. In addition to the third-generation system, an X-ray CT apparatus of a second-generation system and an X-ray CT apparatus of a multislice system are available, which are shown in FIGS. 10A and 10B and FIGS. 11A and 11B. In the second-generation system, the measurement object 2 is moved along the direction of an arrow while being rotated and thus the measurement object 2 with a large size can be imaged. In the multislice system, radiation detectors are arranged in the vertical direction as well as the horizontal direction in the detector 3 and thus a plurality of cross sections can be imaged at the same time. It is easy to assume that the imaging method of the present invention is also applicable to these imaging systems.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An imaging method in an industrial X-ray CT apparatus for transmitting an X-ray emitted from an X-ray source through a measurement object including two substances having different attenuation factors, detecting intensity of X-ray transmitted through the measurement object by a detector and constructing a three-dimensional image from a plurality of CT images, each obtained in a slice surface of the measurement object, comprising the steps of:

setting a position for acquiring a CT image in a first slice surface corresponding to a boundary surface of said two substances having different attenuation factors;

moving said X-ray source and said detector to said first slice surface and two or more upper and lower heights in a height direction perpendicular to said first slice surface and detecting intensity of X-ray by said detector at said two or more upper and lower heights of said first slice surface for each CT image to be imaged;

obtaining a rate of intensity change of X-ray in said height direction on the basis of the intensity of X-ray measured at said two or more upper and lower heights of said first slice surface;

correcting the intensity of X-ray measured at said first slice surface on the basis of said rate of intensity change of X-ray; and obtaining a CT image in said first slice surface on the basis of intensity of X-ray corrected.

* * * * *